United States Patent
Ramachandran et al.

(10) Patent No.: US 10,384,994 B2
(45) Date of Patent: Aug. 20, 2019

(54) OPEN-FLASK HYDROBORATION AND THE USE THEREOF

(71) Applicant: Purdue Research Foundation, West Lafayette, IN (US)

(72) Inventors: P Veeraraghavan Ramachandran, West Lafayette, IN (US); Ameya Sanjay Kulkarni, West Lafayette, IN (US); Michael Patrick Drolet, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/680,258

(22) Filed: Aug. 18, 2017

(65) Prior Publication Data

US 2018/0050972 A1 Feb. 22, 2018

Related U.S. Application Data

(60) Provisional application No. 62/377,146, filed on Aug. 19, 2016.

(51) Int. Cl.
| | |
|---|---|
| *C07C 29/48* | (2006.01) |
| *C07F 5/02* | (2006.01) |
| *C07C 31/125* | (2006.01) |
| *C07C 31/137* | (2006.01) |
| *C07C 33/20* | (2006.01) |
| *C07C 43/13* | (2006.01) |
| *C07C 41/26* | (2006.01) |
| *C07C 31/36* | (2006.01) |
| *C07F 7/18* | (2006.01) |
| *C07C 31/135* | (2006.01) |
| *C07C 31/27* | (2006.01) |
| *C07C 29/03* | (2006.01) |

(52) U.S. Cl.
CPC .............. *C07C 29/48* (2013.01); *C07C 29/03* (2013.01); *C07C 31/125* (2013.01); *C07C 31/137* (2013.01); *C07C 31/1355* (2013.01); *C07C 31/27* (2013.01); *C07C 31/36* (2013.01); *C07C 33/20* (2013.01); *C07C 41/26* (2013.01); *C07C 43/13* (2013.01); *C07F 5/027* (2013.01); *C07F 7/1804* (2013.01); *C07F 7/1876* (2013.01); *C07C 2601/14* (2017.05); *C07C 2602/20* (2017.05); *C07C 2602/42* (2017.05); *C07C 2602/44* (2017.05)

(58) Field of Classification Search
None
See application file for complete search history.

(56) References Cited

PUBLICATIONS

Vedejs et al. Journal of the American Chemical Society, 2005, 127(16), 5766-5767.*
Yang et al. Chem Commun, 2011, 47, 2053-2055.*
H.C. Brown, et al., "Hydroboration. I. The Reaction of Olefins with Sodium Borohydride-Aluminum Chloride." J. Am. Chem. Soc. 1959, 81, 6423-6428.
A. Prokofjevs, et al., "Borenium Ion Catalyzed Hydroboration of Alkenes with N Heterocyclic Carbene-Boranes." J. Am. Chem. Soc. 2012, 134, 12281-12288.
X. Pan, et al., "Molecular Iodine Initiates Hydroborations of Alkenes with N-Heterocyclic Carbene Boranes." J. Am. Chem. Soc. 2013, 135, 14433-14437.
H.I. Schlesinger, et al., "Hydrides of Boron. V. The Ethyl and n-Propyl Diboranes." J. Am. Chem. Soc. 1936, 58, 407-409.
P.C. Moews, et al., "The Reactions between Tetramethyldiborane and Ammonia." Inorganic Chemistry, 1966, 5, 1522-1556.
R.A. Bartlett, et al., "Synthesis and Spectroscopic and Structural Characterization of the Novel Lithium Borylamide Salts." J. Am. Chem. Soc. 1988, 110, 446-449.
X. Chen, et al., "Experimental and Computational Study of the Formation Mechanism of the Diammoniate of Diborane: The Role of Dihydrogen Bonds" J. Am. Chem. Soc. 2011, 133, 14172-14175.
W.J. Shaw, et al., "In Situ Multinuclear NMR Spectroscopic Studies of the Thermal Decomposition of Ammonia Borane in Solution." Angew. Chem. Int. Ed. 2008, 47, 7493-7496.

\* cited by examiner

*Primary Examiner* — Clinton A Brooks
(74) *Attorney, Agent, or Firm* — Purdue Research Foundation; Liang Zeng Yan

(57) ABSTRACT

The present disclosure generally relates to a process for hydroboration of an alkene or alkyne using ammonia borane (AB). In particular, the present invention relates to hydroboration of an alkene or alkyne in the presence of air or moisture, and a clean process for facile preparation of an alcohol by oxidizing the organoborane so formed with hydrogen peroxide. The products, including aminodialkylboranes, ammonia trialkylborane complexes, as well as various alcohols so prepared, are within the scope of this disclosure.

10 Claims, No Drawings

OPEN-FLASK HYDROBORATION AND THE USE THEREOF

CROSS-REFERENCE TO RELATED APPLICATIONS

The present U.S. patent application is related to and claims the priority benefit of U.S. Provisional Patent Application Ser. No. 62/377,146, filed Aug. 19, 2016, the contents of which are hereby incorporated by reference in their entirety into the present disclosure.

TECHNICAL FIELD

The present disclosure generally relates to a process for hydroboration of an alkene or alkyne using ammonia borane (AB). In particular, the present invention relates to hydroboration of an alkene or alkyne in the presence of air or moisture, and a clean process for facile preparation of an alcohol by oxidizing the organoborane so formed with hydrogen peroxide. The intermediate products, including aminodialkylboranes, ammonia trialkylborane complexes, as well as various alcohols so prepared, are within the scope of this disclosure.

BACKGROUND

This section introduces aspects that may help facilitate a better understanding of the disclosure. Accordingly, these statements are to be read in this light and are not to be understood as admissions about what is or is not prior art.

The landmark discovery of ether-catalyzed addition of diborane to olefins (Brown and Rao, *J. Am. Chem. Soc.* 1959, 81, 6428) followed by the introduction of a variety of hydroborating agents, such as borane-tetrahydrofuran (BTHF), borane-dimethyl sulfide (BMS), catecholborane, 9-BBN, etc., transformed organic synthesis (Prokofjevs, et al., *J. Am. Chem. Soc.* 2012, 134, 12281; Pan, et al., *J. Am. Chem. Soc.* 2013, 135, 14433). However, the necessity for strictly anhydrous conditions while handling these reagents, the low molarity and long-term instability of BTHF, and the stench of BMS are some of the drawbacks. The reactions are usually performed under strict anhydrous conditions avoiding contact with air and moisture. A convenient procedure to conduct these experiments in open-flask using reagent-grade laboratory solvents will tremendously increase the utility of this important reaction and pave way for new discoveries.

SUMMARY OF THE INVENTION

Disclosed herein is a novel hydroboration procedure using ammonia borane, which can be conducted in open-flask conditions. In particular, the present invention relates to hydroboration of an alkene or alkyne in the presence of air or moisture, and a clean process for facile preparation of an alcohol by oxidizing the organoborane so formed with hydrogen peroxide. The intermediate products, including aminodialkylboranes, ammonia trialkylborane complexes, as well as various alcohols so prepared, are within the scope of this disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

Disclosed herein is a novel hydroboration procedure using ammonia borane, which can be conducted in open-flask conditions. In particular, the present invention relates to hydroboration of an alkene or alkyne in the presence of air or moisture, and a clean process for facile preparation of an alcohol by oxidizing the organoborane so formed with hydrogen peroxide. The intermediate products, including aminodialkylboranes, ammoniatrialkylborane complexes, as well as various alcohols so prepared, are within the scope of this disclosure.

In some illustrative embodiments, this present invention relates to a process for hydroboration of an alkene or alkyne, comprising the steps of
  a. Preparing a solution of an ammonia borane (AB);
  b. Adding an alkene or alkyne to said AB solution; and
  c. Refluxing with heating and stirring to afford an organoborane intermediate(with concurrent disappearance of AB), wherein the effectiveness of this process is not affected by the presence of air or moisture.

In some illustrative embodiments, this present invention relates to a process for hydroboration of an alkene or alkyne, wherein the solution of an ammonia borane is prepared using an ethereal solvent.

In some illustrative embodiments, this present invention relates to a process for hydroboration of an alkene or alkyne, wherein said ethereal solvent is THF (tetrahydrofuran).

In some illustrative embodiments, this present invention relates to a process for hydroboration of an alkene or alkyne, wherein the solution of an ammonia borane in THF has a concentration of about 0.5~2 M (moles/liter).

In some illustrative embodiments, this present invention relates to a process for hydroboration of an alkene or alkyne, wherein said refluxing is performed at about 90° C.

In some illustrative embodiments, this present invention relates to a process for hydroboration of an alkene or alkyne, wherein said alkene or alkyne is part of an aromatic molecule, an aliphatic molecule, or a combination thereof.

In some illustrative embodiments, this present invention relates to a process for hydroboration of an alkene or alkyne, wherein said alkene or alkyne is part of a cyclic structure, a linear structure, or a combination thereof.

In some illustrative embodiments, this present invention relates to a process for hydroboration of an alkene or alkyne, wherein the molar ratio of said AB to said alkene or alkyne ranges from about 2 to about 0.2.

In some illustrative embodiments, this present invention relates to an aminodialkylborane or ammonia-trialkylborane prepared according to the process of
  a. Preparing a solution of an ammonia borane (AB);
  b. Adding an alkene or alkyne to said AB solution; and
  c. Refluxing with heating and stirring to afford an organoborane (with concurrent disappearance of AB), wherein the effectiveness of this process is not affected by the presence of air or moisture.

In some illustrative embodiments, this present invention relates to an aminodialkylborane or ammonia-trialkylborane complex prepared according to the process disclosed herein, wherein the solution of an ammonia borane is prepared using THF (tetrahydrofuran).

In some illustrative embodiments, this present invention relates to an aminodialkylborane or ammonia-trialkylborane complex prepared according to the process disclosed herein, wherein the solution of an ammonia borane in THF has a concentration of about 0.5~2 M (moles/liter).

In some illustrative embodiments, this present invention relates to an aminodialkylborane or ammonia-trialkylborane complex prepared according to the process disclosed herein, wherein said refluxing is performed at about 90° C.

In some illustrative embodiments, this present invention relates to an aminodialkylborane or ammonia-trialkylborane complex prepared according to the process disclosed herein, wherein said alkene or alkyne is part of an aromatic molecule, an aliphatic molecule, or a combination thereof.

In some illustrative embodiments, this present invention relates to an aminodialkylborane or ammonia-trialkylborane complex prepared according to the process disclosed herein, wherein said alkene or alkyne is part of a cyclic structure, a linear structure, or a combination thereof.

In some illustrative embodiments, this present invention relates to an aminodialkylborane or ammonia-trialkylborane complex prepared according to the process disclosed herein, wherein the molar ratio of said AB to said alkene or alkyne ranges from about 2 to about 0.2.

In some illustrative embodiments, this present invention relates to a process for preparing a primary or secondary alcohol, or vicinal diol using an alkene or alkyne, respectively, comprising the steps of
  a. Preparing a solution of an ammonia borane (AB);
  b. Adding an alkene or alkyne to said AB solution;
  c. Refluxing with heating and stirring to afford an organoborane (with concurrent disappearance of AB), wherein the effectiveness of this process is not affected by the presence of air or moisture;
  d. Cooling the reaction mixture to about 0° C. and then adjusting the pH of the solution to basic with a NaOH solution; and
  e. Oxidizing said organoborane by adding about three equivalents of $H_2O_2$ to afford an alcohol.

In some illustrative embodiments, this present invention relates to a process for preparing a primary or secondary alcohol, or diol using an alkene or alkyne, wherein the molar ratio of said AB to said alkene or alkyne ranges from about 2 to about 0.2.

In some illustrative embodiments, this present invention relates to a process for preparing a vicinal diol using an alkyne, wherein the molar ratio of said AB to said alkyne is about 2.

In some illustrative embodiments, this present invention relates to a process for preparing a primary or secondary alcohol using an alkene, wherein the molar ratio of said AB to said alkene is about 0.3.

In some illustrative embodiments, this present invention relates to a process for preparing a primary or secondary alcohol using an alkene, wherein the molar ratio of said AB to said alkene is about 0.5.

The following examples and specific embodiments are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

The required ammonia borane was prepared in large-scale from sodium borohydride (SBH) and powdered ammonium sulfate in reagent grade THF containing 5% dissolved ammonia at ambient temperature and pressure (Scheme 1).

Scheme 1. Synthesis of ammonia borane in ammoniated THF.

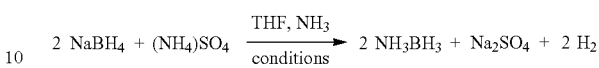

Ammonia borane (AB) with its strong B—N bond did not hydroborate alkenes at room temperature. It was found that AB could be used for the hydroboration of olefins in refluxing tetrahydrofuran. Terminal olefins were converted to the corresponding trialkylborane-ammonia complex ($R_3B$—$NH_3$) and internal di- and tri-substituted olefins were converted to $R_2B$—$NH_2$ (Scheme 2).

Scheme 2. Hydroboration using ammonia borane.

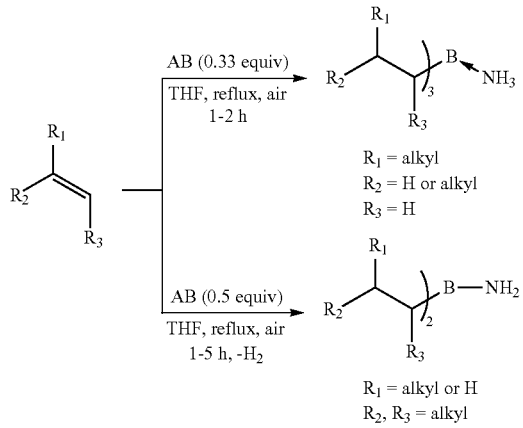

The project was begun by treating 1-octene (2a) with 0.33 equiv. of AB in 1 M THF at room temperature (rt) when no reaction was observed. Refluxing the reaction contents for 1 h revealed complete consumption of AB and a sharp singlet at δ-6 ppm, by $^{11}$B NMR spectroscopy. Notably, none of the AB dehydrogenation products were observed, similar to the nucleophilic displacement reaction. The high field resonance of the initial product peak indicated a tetra-coordinated boron, probably an ammonia-trioctylborane complex (3a). Although stable under the reaction conditions, efforts to isolate the product by complete evaporation of the solvent in vacuo led to its degradation.

In another reaction, after an hour of reflux, an equivalent of $BF_3$-$Et_2O$ was added to the reaction mixture. The δ-6 ppm peak in the $^{11}$B NMR spectrum shifted to δ 80 ppm (trioctylborane), with an additional peak at δ-1 ppm ($BF_3$—$NH_3$) corroborating our presumption that ammonia remained complexed in the product. For further verification, a reaction was conducted in THF-$d_8$ wherein analysis by $^1$H NMR spectroscopy revealed complete consumption of all three equiv. of 1-octene upon reflux for 1 h. Moreover, alkaline hydrogen peroxide oxidation of 3a yielded 89% of octanol (4a) validating that all three equivalents of olefin have been hydroborated (Table 1, entry 1). Significantly, the ratio of the 1°-(primary) and 2°-(secondary) isomers of the alcohol is 98:2, compared to 94:6 obtained with BTHF or BMS.[18] Considering that this ratio is a combination of the regioselectivities achieved over three separate hydroboration steps, it can be assumed that the first hydroboration step occurs with superior regioselectivity compared to that with BTHF or BMS.

Probing the reaction for concentration, temperature, and solvent, revealed refluxing THF at a concentration of about 2 M with respect to AB as optimal. Hydroboration-oxidation of a variety of terminal olefins was then undertaken (Table 1). 1-Decene (2b), after 1 h reflux, followed by oxidation yielded 90% of decanol (4b) in a 97:3 ratio of the 1°- and 2°-isomers (entry 2). A 2,2-disubstituted terminal olefin (2-methyloct-1-ene, 2c) and an exo-methylene cycloalkene (β-pinene, 2d) led to the formation of the corresponding ammonia-trialkylboranes, 3c and 3d, respectively (entries 3-4). Unlike 3a, these complexes began to dissociate to the trialkylborane ($^{11}$B NMR: δ 80 ppm) before the complete consumption of AB. Justifiably, the stability of trialkylborane-ammonia complexes is governed by the steric environment around boron. Oxidation of 3c and 3d yielded 77% and 71% of the corresponding alcohol 4c and cis-myrtanol (4d), respectively. Styrene (2e) yielded 83% of phenethanol (4e), as a 4:1 mixture of internal and terminal alcohols (entry 5), similar to that obtained with BTHF. Olefins containing heteroatoms (2f, 2g, and 2h) also underwent hydroboration-oxidation to provide the alcohols in good to high yields and excellent regioselectivities (entries 6-8).

TABLE 1

Hydroboration-Oxidation of Terminal Alkenes[a]

| Entry | Olefin (2) | Time (h) | Alcohol (4) | Yield[b] (%) | 1°:2°[c] |
|---|---|---|---|---|---|
| 1 | C$_6$H$_{13}$— (2a) | 1 | 4a | 89 | 98:2 |
| 2 | C$_8$H$_{17}$— (2b) | 1 | 4b | 90 | 97:3 |
| 3 | C$_6$H$_{13}$— (2c) | 4 | 4c | 77 | 99:1 |
| 4 | (2d, β-pinene) | 1 | 4d | 71 | 93:7 |
| 5 | (2e, styrene) | 1 | 4e | 94 | 80:20 |
| 6 | (2f) | 3 | 4f | 59 | >99:1 |
| 7 | Br— (2g) | 1 | 4g | 78 | >99:1 |
| 8 | TBSO— (2h) | 1 | 4h | 81 | 98:2 |

[a]All of the reactions were conducted using 5 mmol AB and 15 mmol of the alkene in 2.5 mL THF under open-flask conditions.
[b]Yield of the isolated alcohol.
[c]Ascertained by $^1$H NMR spectroscopy.

Surprisingly, an internal alkene, cis-2-butene (2i), after 4 h reflux with 0.33 equiv. of AB, revealed a major singlet significantly downfield at δ 48 ppm, along with the expected resonances for the ammonia-tri-sec-butylborane (δ-6 ppm) and unreacted AB (δ-22 ppm). To clarify this deviation from the hydroboration of terminal alkenes, a higher boiling substrate, cyclohexene (2j), was hydroborated with 0.5 equiv of AB. After 1 h reflux, all of the AB was consumed with a concurrent gas evolution. Similar to cis-2-butene hydroboration, analysis by $^{11}$B NMR spectroscopy showed a major singlet at δ 48 ppm and a minor peak at δ-6 ppm (ammonia-tricyclohexylborane). Unlike the hydroboration of terminal alkenes, the product could be isolated in 95% yield (Table 2, entry 1), which was determined to be aminodicyclohexylborane (5j) by NMR and HRMS techniques. Further purification was possible by distillation (77% yield). Though stable under the reaction conditions, 5j must be stored under an inert atmosphere to prevent hydrolysis. Thus, the first metal-free one-pot hydroboration-dehydrogenation sequence with direct access to the difficult to prepare aminodialkylboranes (5) has been realized (Scheme 3). Current approaches to 5 are multi-step and involve the use of non-commercial, highly pyrophoric, and moisture-sensitive reactants. These include (i) the treatment of tetramethyldiborane with ammonia (Schlesinger, et al., *J. Am. Chem. Soc.*, 1936, 58, 409; Moews, et al., *Inorg. Chem.*, 1966, 5, 1522) and (ii) preparation of dialkylborane derivatives, followed by amine exchange (Bartlett, et al., *J. Am.*

Chem. Soc., 1988, 110, 446; Goates, et al., J. Chem. Soc. 1961, 4909). Thus, our open-flask one-pot hydroboration-dehydrogenation sequence represents a significant improvement over the current routes to aminodialkylboranes. We believe that the sequence proceeds via the thermally unstable ammonia-dialkylborane intermediate. Oxidation of 5j yielded cyclohexanol in 80% yield.

Scheme 3: Routes to aminodialkylboranes.

Prior approaches to aminodialkylboranes:
a) From tetramethyldiborane (see text for ref.)

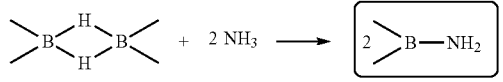

b) From dialkylborane derivatives (see text for ref.)

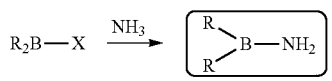

This work: "Metal-free" tandem hydroboration-dehydrogenation

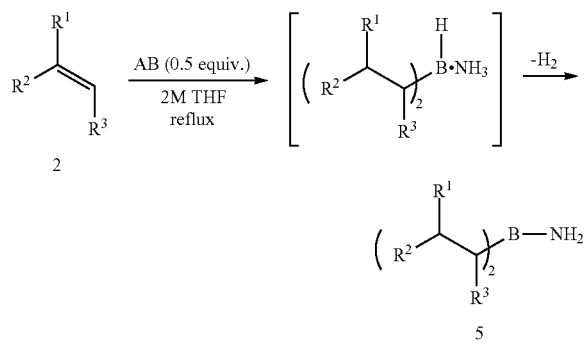

A series of internal olefins were then hydroborated to obtain the corresponding aminodialkylboranes (5) and, after oxidation, the alcohols (4) in high yields and purity (Table 2). Norbornene (2k) furnished 99% of aminodi-exo-norbornylborane (5k) selectively (entry 2). (Z)-hept-3-ene (2l) yielded the corresponding aminodialkylborane (5l) in 97% yield, albeit as a 1:1 mixture of 4- and 3-substituted products (entry 3), and (Z)-oct-4-ene (2m) afforded aminodi(octan-4-yl)borane (5m) in 95% yield (entry 4). Trisubstituted olefins, 2-methylpent-2-ene (2n) and 1-methylcyclohexene (2o) also underwent hydroboration-dehydrogenation providing the corresponding aminodialkylboranes 5n and 5o, respectively in 92% and 97% yields (entries 5-6). In all of the above cases, the aminodialkylboranes were essentially pure and necessitated no purification. Cyclic trisubstituted olefins, (+)-α-pinene (2p), and (+)-3-carene (2q)) were refluxed with AB to yield 92% of aminodiisopinocampheylborane (5p) and 97% of aminodiiso-4-caranylborane (5q), respectively (entries 7-8). While 5q was pure, 5p was obtained as a 95:5 mixture with the ammonia-trialkylborane complex, which could be purified.[20]

Oxidation of all of the above aminodialkylboranes (5) provided the corresponding 2°-ols (4) in high yields (Table 2). Attempted preparation of the ammonia-trialkylborane complexes from two representative internal olefins (2j and 2p), despite being used in excess (3-5 equiv), yielded the aminodialkylborane as the predominant product. Efforts to selectively prepare aminodialkylboranes from terminal olefins using two equiv. olefin also failed.[20] A representative tetrasubstituted olefin, 2,3-dimethylbut-2-ene (2r), after 4 h reflux, provided a mixture of ammonia-thexylborane and its dehydrogenation products, including B-alkylsubstituted borazine.

TABLE 2

Synthesis of Aminodialkylboranes (5)[a]

| Entry | Olefin (2) | Time (h) | Ratio[b] (5:3) | Yield (%) 5 | 4[c] |
|---|---|---|---|---|---|
| 1 | 2j | 1 | 90:10 | 95 (77)[d] | 80 |
| 2 | 2k | 1 | >99:<1 | 99 | 81 |
| 3 | 2l (C3H7, C2H5) | 2 | >99:<1 | 97 | 87 |
| 4 | 2m (C3H7, C3H7) | 1 | >99:<1 | 95 | 72 |
| 5 | 2n | 3 | >99:<1 | 92 | 87 |
| 6 | 2o | 1 | >99:<1 | 97 | 87 |
| 7 | 2p | 1 | 95:5 | 92[e] | 98[f] |
| 8 | 2q | 3 | >99:<1 | 97 | 84 |

[a]All of the reactions were conducted using 5 mmol AB and 10 mmol of the alkene in 2.5 mL THF.
[b]Ascertained by $^{11}$B NMR spectroscopy.
[c]Yield of the isolated alcohols (4) after alkaline hydrogen peroxide oxidation.
[d]Yield in parenthesis after distillation.
[e]After precipitation of ammonia-trialkylborane complex.
[f]The enantiomeric excess of the olefin was retained in the product.

Although tremendous progress has been made with regard to the applications of conventional uncatalyzed hydroboration, conflicting opinions exist regarding its mechanism. NH₃ remains complexed to the product after hydroboration with AB, pointing to a mechanism wherein the Lewis base may not be fully dissociated. This could be envisioned via a nucleophilic attack of the olefin on AB leading to an $S_N2$-like transition state with association of NH₃ to the boron center. Alternatively, for a dissociative hydroboration-recomplexation to occur, the gaseous NH₃ should remain trapped in a solvent cage at elevated temperatures in refluxing THF, which is unlikely. Assuming loss of even traces of ammonia, the presence of BTHF or free trialkylborane should be observed. Neither was detected by ¹¹B NMR spectroscopy supporting a non-dissociative hydroboration.

Apart from those discussed above, other pathways also could be implicated in hydroboration with AB. Autrey and coworkers have reported the isomerization of AB to diammoniate of diborane (DADB) prior to dehydrogenation in glyme at 80° C. (Shaw, et al., *Angew. Chem., Int. Ed.*, 2008, 47, 7493). On this basis, hydroboration via the intermediacy of DADB is a possibility. However, no DADB was observed during the course of our experiments. Likewise, the precursor to DADB, ammonia diborane (AaDB) was also not observed in the ¹¹B NMR spectrum (Chen, et al., *J. Am. Chem. Soc.*, 2011, 133, 14172).

In summary, a convenient, open-air hydroboration protocol using AB in refluxing THF has been described. This is the first report of an uncatalyzed hydroboration wherein the Lewis base (ammonia) is retained in the product. This safe alternative to traditional hydroboration provides either trialkylborane-ammonia complexes from terminal alkenes or aminodialkylboranes from internal alkenes. Oxidation of these hydroboration products provides the corresponding alcohols in high yields. The high borane content (45%) and air-stability of AB are major advantages to this protocol.

Another important extension of alkene hydroboration is alkyne hydroboration, which provides an facile route to vicinal diols as showing in Scheme 4 below.

Scheme 4. Hydroboration of Alkyne and Oxidation to Prepare vicinal diols

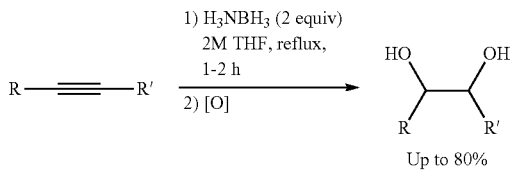

Up to 80%

According Scheme 5, diol product 16a was obtained at an isolated yield of 78% from diphenylacetylene 14a using two equivalents of ammonia borane. On the other hand, in situ generation of ammonia borane from sodium borohydride and ammonium sulfate in THF under refluxing, 83% of diol product 16a was isolated.

Scheme 5. Preparation of Diol 16a

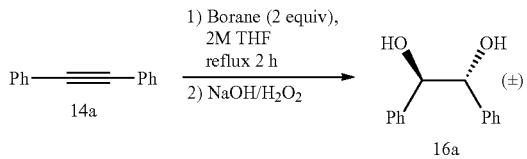

Experimental Procedures

General Considerations Unless otherwise noted, all reactions were carried out in dry glassware open to air. All solvents were used as received commercially. ¹H, ¹³C, and ¹¹B NMR spectra were recorded at room temperature on a Varian INOVA 300 MHz NMR spectrophotometer. Chemical shifts (δ values) are reported in parts per million (ppm) and are referenced to BF₃-Et₂O for ¹¹B NMR. Data are reported as: δ value, multiplicity (s=singlet, d=doublet, t=triplet, q=quartet, m=multiplet, br=broad) and integration. HRMS data were collected on a FinniganMAT XL95 spectrometer via direct probe injection. All olefins were purchased from commercial sources and were distilled before use. Ammonia borane (AB, 1) was synthesized via our previously reported procedure. Avoid contact with easily reduced, flammable compounds (e.g. acetone), which may combust upon contact with AB.

Optimization of Reaction Conditions with oct-1-ene (Table 3): The reaction was extremely slow (¹¹B NMR spectroscopy) until the mixture reached reflux (THF). Solvent concentration was targeted first for optimization with the stoichiometry being 3:1 for 1-octene:AB (Table 3, Entries 1-3). Reactions at a concentration of 2 M in tetrahydrofuran (THF) provided with respect to AB provided the highest yields for octanol. At 4 M, addition of the olefin resulted in precipitation of AB, generating a heterogeneous reaction mixture. Stoichiometry of oct-1-ene to AB was optimized at 2 M in THF. At 1:1 equivalency (Entry 4), significant amounts of AB degradation products were observed. At 2:1 equivalency (Entry 5), a mixture of aminodioctylborane to trioctylborane-ammonia complex was observed in a ratio of approximately 60:40, which could not be purified. An equivalency of 3:1 cleanly provided a single signal at δ-6 ppm and was chosen for further optimization (Entry 6). AB was seen to be essentially insoluble in dichloromethane, diethyl ether, pentane, or neat in oct-1-ene (Entries 6-9). After extended reaction times and subsequent oxidation, only trace amounts of octan-1-ol were observed. Acetonitrile was found to give similar results to THF without any reaction with the solvent (Entry 10).

TABLE 3

Optimization of hydroboration of oct-1-ene with ammonia borane.

| Entry | Solvent | Concentration (M) | Equiv. Olefin | Time (h) | Yield (%) |
|---|---|---|---|---|---|
| 1 | THF | 1 | 3 | 1 | 84 |
| 2 | THF | 2 | 3 | 1 | 89 |
| 3 | THF | 4 | 3 | 1 | 89 |
| 4 | THF | 2 | 1 | 5 | 92 |
| 5 | THF | 2 | 2 | 2 | 88 |
| 6 | CH₂Cl₂ | 2 | 3 | 19 | Trace |
| 7 | Et₂O | 2 | 3 | 19 | Trace |
| 8 | Pentane | 2 | 3 | 19 | Trace |
| 9 | neat | 2 | 3 | 22 | Trace |
| 10 | CH₃CN | 2 | 3 | 2 | 89 |

Representative procedure for the synthesis of ammonia-trialkylboranes (3) and oxidation to alcohols (4).

To a dry 25 mL round bottom flask containing a magnetic stir bar was added 0.154 g ammonia borane (5 mmol, 1 equiv.), 2.5 mL THF, and 2.4 mL 1-octene (15 mmol, 3 equiv.). The flask was fitted with a water-cooled reflux condenser and the reaction mixture rapidly brought to reflux in an oil bath at 90° C. The reaction was stirred for 1 h open to air, after which time an aliquot was analyzed by $^{11}$B NMR spectroscopy, which showed complete disappearance of the peak due to AB and a new singlet at δ-6 ppm. The reaction mixture was cooled in an ice-water bath and oxidized with the dropwise addition of 1.7 mL 3 M NaOH (5 mmol, 1 equiv), followed by the dropwise addition of 1.7 mL 30% $H_2O_2$ (15.5 mmol, 3.1 equiv). The reaction contents were allowed to warm to room temperature with continued stirring for 3 h. The reaction mixture was extracted with diethyl ether and the combined organic extracts washed with brine, dried over sodium sulfate, and concentrated in vacuo to furnish 1.74 g of octanol (4a) in 89% yield. The ratio of the primary and secondary alcohols was determined by $^1$H NMR as 98:2.

Representative procedure for the synthesis of essentially pure aminodialkylboranes (5k-5o and 5q).

Caution: Due to the liberation of flammable hydrogen gas, the reactions were carried out in a well-ventilated hood. Following a similar procedure as above, 1.6 mL (+)-3-carene (2q) (10 mmol, 2 equiv), 0.154 g ammonia borane (5 mmol, 1 equiv), and 2.5 mL THF were refluxed under nitrogen for 1 h, after which time the reaction mixture was analyzed by $^{11}$B NMR spectroscopy to show a peak at δ 48 ppm. Removal of solvent in vacuo yielded 1.486 g of aminodi-4-isocaranylborane (5q) as a slightly turbid, viscous liquid in 97% yield. Oxidation of 5 was carried out as with ammonia-trialkylborane complexes (3).

Large scale preparation of aminodicyclohexylborane (5j). Purification by distillation.

Following a similar procedure as above, 10.1 mL cyclohexene (2j) (100 mmol), 1.54 g ammonia borane (50 mmol), and 25 mL THF were refluxed for 1 h, after which time the reaction mixture was analyzed by $^{11}$B NMR spectroscopy to show peaks at δ 48 ppm and δ-6 ppm in a 9:1 ratio. The solvent was removed in vacuo and the organic residue distilled under reduced pressure to yield aminodicyclohexylborane (5j) as a clear, colorless liquid in 77% yield.

Preparation of aminodiisopinocampheylborane (5p). Removal of trialkylborane-ammonia complex.

Following a similar procedure as above, 1.6 mL (+)-α-pinene (2p) (10 mmol, 2 equiv), 0.154 g ammonia borane (5 mmol), and 2.5 mL THF were refluxed for 1 h, after which time the reaction mixture was analyzed by $^{11}$B NMR to show peaks at δ 48 ppm and δ-6 ppm. The solvent was removed in vacuo, and the residue was suspended in 2.5 mL anhydrous pentane, whereupon a white solid formed. The suspension was filtered through a bed of celite and the solid residue washed twice with 2.5 mL pentane. The organic solvent was removed to yield 1.486 g of aminodiisopinocampheylborane (5p) as a clear, colorless, viscous liquid in 92% yield.

Trioctylborane-ammonia (3a), Not isolated. Clear, colorless solution in THF. $^1$H NMR (300 MHz, Tetrahydrofuran-d8) δ 3.41 (s, 3H), 1.26 (s, 30H), 1.16-0.97 (m, 6H), 0.87 (t, J=6.7 Hz, 9H), 0.25--0.02 (m, 6H). $^{13}$C NMR (75 MHz, Tetrahydrofuran-d8); δ 35.84, 33.34, 31.17, 30.80, 27.56, 23.93, 14.98. LRMS (EI) calcd for $C_{24}H_{54}BN$ [M]$^+$: m/z, 367, found 367.

Octan-1-ol (4a), 89% yield. Clear, colorless liquid. $^1$H NMR (300 MHz, CDCl$_3$) δ 3.64 (t, J=6.6 Hz, 2H), 1.56 (m, 2H), 1.42-1.14 (m, 10H), 0.88 (t, J=6.4 Hz, 3H). $^{13}$C NMR (75 MHz, CDCl$_3$) δ 63.25, 33.08, 32.10, 29.63, 29.58, 26.05, 22.96, 14.40.

Decan-1-ol (4b), 90% yield. Clear, colorless liquid. $^1$H NMR (300 MHz, CDCl$_3$) δ 3.55 (t, J=6.7 Hz, 2H), 2.83 (br s, 1H), 1.49 (m, 2H), 1.23 (m, 14H), 0.84 (t, J=6.7 Hz, 3H). $^{13}$C NMR (75 MHz, CDCl$_3$) δ 62.96, 33.00, 32.18, 29.91, 29.74, 29.61, 26.07, 22.96, 14.38.

2-Methyloctan-1-ol (4c), 77% yield. Clear, colorless liquid. $^1$H NMR (300 MHz, CDCl$_3$) δ 3.46 (ddd, J=29.6, 10.5, 6.2 Hz, 2H), 1.70-1.52 (m, 1H), δ 1.48-1.17 (m, 9H), 1.16-1.02 (m, 1H), 0.89 (dd, J=12.7, 6.8 Hz, 6H). $^{13}$C NMR (75 MHz, CDCl$_3$) δ 68.66, 36.06, 33.45, 32.17, 29.91, 27.25, 22.98, 16.91, 14.43.

cis-Myrtanol (4d), 71% yield. Clear, colorless liquid. $^1$H NMR (300 MHz, CDCl$_3$) δ 3.62-3.46 (m, 2H), 2.37 (dt, J=9.5, 6.3 Hz, 1H), 2.31-2.16 (m, 1H), 2.08-1.79 (m, 5H), 1.54-1.37 (m, 1H), 1.19 (s, 3H), 0.97 (s, 3H), 0.93 (d, J=9.6 Hz, 1H). $^{13}$C NMR (75 MHz, CDCl$_3$) δ 67.79, 44.61, 43.13, 41.72, 38.89, 33.45, 28.29, 26.33, 23.67, 19.15.

2-phenylethanol (4e) & 1-phenylethanol (minor) (82:18), 83% yield (combined). Clear, colorless liquid. $^1$H NMR (300 MHz, CDCl$_3$) δ 7.50-6.96 (m, 6H), 4.82 (q, J=6.4 Hz, 0.23H), 3.77 (t, J=6.6 Hz, 2H), 2.81 (t, J=6.7 Hz, 2H), 2.44 (br s, 0.23H), 2.00 (br s, 1H), 1.45 (d, J=6.5 Hz, 0.73H). $^{13}$C NMR (75 MHz, CDCl$_3$) δ 138.57, 129.04, 128.54, 126.47, 125.43, 63.72, 39.36, 25.33.

2-Butoxyethan-1-ol (4f), 59% yield. Clear, colorless liquid. $^1$H NMR (300 MHz, CDCl$_3$) δ 3.71-3.65 (t, 2H), 3.53-3.33 (m, 4H), 2.54 (br. s, 1H), 1.71-1.44 (m, 2H), 1.44-1.14 (m, 2H), 0.88 (m, 3H). $^{13}$C NMR (75 MHz, CDCl$_3$) δ 71.96, 71.05, 70.55, 61.56, 31.70, 26.48, 19.30, 13.94.

5-Bromopentan-1-ol (4g), 78% yield. Colorless liquid; turned yellow then brown over time. $^1$H NMR (300 MHz, CDCl$_3$) δ 3.62 (t, J=6.2 Hz, 2H), 3.42 (t, J=6.7 Hz, 2H), 2.80 (br s, 1H), 1.98-1.77 (m, 2H), 1.68-1.37 (m, 4H). $^{13}$C NMR (75 MHz, CDCl$_3$) δ 62.38, 33.98, 32.63, 31.83, 24.59.

4-(Tert-butyldimethylsilyloxy)butan-1-ol (4h), 81% yield. Clear, colorless liquid. $^1$H NMR (300 MHz, CDCl$_3$) δ 3.67-3.51 (m, 4H), 3.14 (br s, 1H), 1.68-1.51 (m, 4H), 0.85 (d, J=2.5 Hz, 9H), 0.03 (s, 6H). $^{13}$C NMR (75 MHz, CDCl$_3$) δ 63.51, 62.73, 30.23, 30.02, 26.14, 18.55, −5.10.

Aminodicyclohexylborane (5j) 77% yield after distillation in vacuo. Clear, colorless liquid. $^1$H NMR (300 MHz, CDCl$_3$) δ 3.67 (br s, 2H), 1.69 (m, 11H), 1.38-1.16 (m, 6H), 1.15-0.99 (m, 3H), 0.99-0.83 (m, 2H). $^{13}$C NMR (75 MHz, CDCl$_3$) δ 29.47, 28.35, 27.58. $^{11}$B NMR (96 MHz, CDCl$_3$) δ 47.52. HRMS (EI) calcd for $C_{12}H_{24}BN$ [M]$^+$: m/z, 193.1996, found 193.1997.

Cyclohexanol (4j), 67% yield. Pale yellow liquid. $^1$H NMR (300 MHz, CDCl$_3$) δ 3.73-3.52 (m, 1H), 1.89 (m, 2H), 1.81-1.66 (m, 2H), 1.65-1.48 (m, 1H), 1.39 (m, 1H), 1.34-1.05 (m, 5H). $^{13}$C NMR (75 MHz, CDCl$_3$) δ 70.04, 35.48, 25.60, 24.37.

Amino-di-exo-norbornylborane (5k), 99% yield. Clear, colorless viscous liquid. $^1$H NMR (300 MHz, CDCl$_3$) δ 3.51 (br s, 2H), 2.13 (s, 2H), 2.06 (s, 2H), 1.53-1.34 (m, 4H), 1.35-1.06 (m, 8H), 1.02 (s, 4H), 0.87-0.73 (dt, 2H). $^{13}$C NMR (75 MHz, CDCl$_3$) δ 38.72, 38.60, 38.28, 38.20, 37.21, 34.01, 33.94, 33.20, 29.52. $^{11}$B NMR (96 MHz, CDCl$_3$) δ 48.04. HRMS (EI) calcd for $C_{14}H_{24}BN$ [M]$^+$: m/z, 217.1996, found 217.1990.

Exo-2-norborneol (4k), 81% yield. White solid. $^1$H NMR (300 MHz, CDCl$_3$) δ 3.85-3.68 (m, 1H), 2.25 (s, 1H), 2.14 (d, J=3.8 Hz, 1H), 1.71-1.51 (m, 3H), 1.51-1.34 (m, 1H), 1.34-1.20 (m, 1H), 1.12 (ddd, J=9.8, 2.5, 1.4 Hz, 1H), 1.07-0.96 (m, 2H). $^{13}$C NMR (75 MHz, CDCl$_3$) δ 75.13, 44.56, 42.59, 35.68, 34.66, 28.38, 24.70.

Aminodiheptylboranes (5l), 97% yield as mixture of three potential compounds (3,3' or 4,4' or 3,4'). Slightly turbid, colorless, viscous liquid. $^1$H NMR (300 MHz, CDCl$_3$) δ 3.69 (br s, 2H), 1.50-1.13 (m, 16H), 1.04-0.76 (m, 14H). $^{13}$C NMR (75 MHz, CDCl$_3$) δ 34.50, 33.25, 31.82, 31.35, 24.60, 23.67, 23.28, 22.69, 15.04, 14.50, 14.04. $^{11}$B NMR (96 MHz, CDCl$_3$) δ 49.25.

Heptan-3-ol and heptan-4-ol (1:1 mixture) (4l), 87% yield. Clear, colorless liquid. $^1$H NMR (300 MHz, CDCl$_3$) δ 3.60 (m, 1H), 3.57-3.45 (m, 1H), 1.77 (br s, 2H), 1.62-1.19 (m, 16H), 0.93 (d, J=3.8 Hz, 12H). $^{13}$C NMR (75 MHz, CDCl$_3$) δ 73.44, 71.57, 39.97, 36.94, 30.44, 28.21, 23.15, 19.21, 14.51, 10.29.

Aminodioct-4-ylborane (5m), 95% yield. Slightly turbid, colorless, viscous liquid. $^1$H NMR (300 MHz, CDCl$_3$) δ 3.66 (s, 2H), 1.41-1.10 (m, 21H), 0.87 (m, 13H). $^{13}$C NMR (75 MHz, CDCl$_3$) δ 34.54, 31.89, 31.77, 23.67, 22.69, 15.03, 14.49. $^{11}$B NMR (96 MHz, CDCl$_3$) δ 48.95. LRMS (APCI) calcd for C$_{16}$H$_{36}$BN [M-H]$^-$: m/z, 253.3, found 253.3.

Octan-4-ol (4m), 72% yield. Clear, colorless liquid. $^1$H NMR (300 MHz, CDCl$_3$) δ 3.68-3.51 (m, 1H), 2.55-2.31 (br s, 1H), 1.57-1.22 (m, 9H), 0.98-0.84 (m, 5H). $^{13}$C NMR (75 MHz, CDCl$_3$) δ 71.61, 39.82, 37.35, 28.08, 22.99, 19.05, 14.30, 14.25.

Aminodi(2-methylpent-3-yl)borane (5n), 92% yield. Slightly turbid, colorless, viscous liquid. $^1$H NMR (300 MHz, CDCl$_3$) δ 3.80 (br s, 2H), 1.85-1.56 (m, 2H), 1.53-1.15 (m, 4H), 1.00-0.76 (m, 20H). $^{13}$C NMR (75 MHz, CDCl$_3$) δ 28.60, 28.23, 24.12, 23.37, 21.32, 21.21, 20.51, 20.38, 14.39, 13.81. $^{11}$B NMR (96 MHz, CDCl$_3$) δ 56.40 (borinic acid), 48.74 (major), 34.15 (boronic acid), 17.67 (boric acid), 0.26. LRMS (APCI) calcd for C$_{12}$H$_{28}$BN [M]$^+$: m/z, 197.2, found 197.3. HRMS (EI) calcd for C$_{12}$H$_{27}$BO [M]$^+$: m/z, 198.2149, found 198.2150 (hydrolysis product).

2-Methylpentan-3-ol (4n), 87% yield. Clear, colorless liquid. $^1$H NMR (300 MHz, CDCl$_3$) δ 3.26 (m, 1H), 2.24 (br s, 1H), 1.67-1.52 (m, 1H), 1.57-1.46 (m, 1H), 1.44-1.33 (m, 1H), 0.88 (t, J=7.5 Hz, 3H), 0.84 (d, J=6.8 Hz, 6H). $^{13}$C NMR (75 MHz, CDCl$_3$) δ 78.23, 33.23, 27.01, 19.08, 17.37, 10.52.

Aminodi-2-methylcyclohexylborane (5o), 97% yield. Clear, colorless, viscous liquid. $^1$H NMR (300 MHz, CDCl$_3$) δ 3.65 (br s, 2H), 1.80-1.55 (m, 12H), 1.41-0.87 (m, 6H), 0.83 (d, J=6.5 Hz, 6H), 0.58 (ddd, J=23.7, 12.2, 2.8 Hz, 2H). $^{13}$C NMR (75 MHz, CDCl$_3$) δ 77.66, 77.24, 76.81, 39.23, 37.17, 37.05, 34.85, 34.18, 30.17, 29.76, 28.03, 27.81, 27.44, 23.60, 23.48, 1.42. $^{11}$B NMR (96 MHz, CDCl$_3$) δ 48.56.

Trans-2-methylcyclohexanol (4o), 87% yield. Clear, colorless liquid. $^1$H NMR (300 MHz, CDCl$_3$) δ 3.17-3.05 (dt, 1H), 1.94 (m, 1H), 1.82-1.45 (m, 4H), 1.25 (m, 5H), 1.01 (d, J=6.4 Hz, 3H). $^{13}$C NMR (75 MHz, CDCl$_3$) δ 76.09, 40.11, 35.47, 33.81, 25.78, 25.31, 18.75.

Aminodiisopinocampheylborane (5p), 92% yield after precipitation of triisopinocampheylborane-ammonia complex. Clear, colorless, viscous liquid. $^1$H NMR (300 MHz, CDCl$_3$) δ 3.60 (br s, 2H), 2.24 (ddd, J=15.4, 6.2, 2.0 Hz, 2H), 1.98 (ddt, J=8.3, 4.9, 2.1 Hz, 6H), 1.76-1.68 (m, 2H), 1.53 (ddd, J=13.1, 8.1, 2.4 Hz, 2H), 1.28 (dt, J=10.8, 8.2 Hz, 2H), 1.12 (s, 6H), 1.03 (s, 6H), 0.90 (d, J=7.1 Hz, 6H), 0.63 (d, J=9.3 Hz, 2H). $^{13}$C NMR (75 MHz, CDCl$_3$) δ 48.66, 42.10, 39.06, 35.02, 30.89, 28.92, 23.62, 23.12. $^{11}$B NMR (96 MHz, CDCl$_3$) δ 47.81, −4.65. HRMS (EI) calcd for C$_{20}$H$_{36}$BN [M]$^+$: 301.2935, found 301.2937.

(−)-Isopinocampheol (4p), 98% yield. Pale yellow crystals. $^1$H NMR (300 MHz, CDCl$_3$) δ 4.07 (dt, J=9.6, 5.0 Hz, 1H), 2.59-2.44 (m, 1H), 2.44-2.31 (m, 1H), 2.01-1.87 (m, 2H), 1.80 (dt, J=5.9, 1.9 Hz, 1H), 1.71 (ddd, J=13.9, 4.7, 2.6 Hz, 1H), 1.57 (s, 1H), 1.28-1.18 (m, 3H), 1.12 (t, J=8.0 Hz, 3H), 1.09-0.98 (m, 1H), 0.95 (d, J=16.9 Hz, 3H). $^{13}$C NMR (75 MHz, CDCl$_3$) δ 71.09, 47.90, 47.32, 41.84, 38.88, 38.27, 34.28, 27.80, 23.81, 20.87.

Aminodi-4-isocaranylborane (5q), 97% yield. Clear, colorless, viscous liquid. $^1$H NMR (300 MHz, CDCl$_3$) δ 3.51 (br s, 2H), 2.03-1.80 (m,2), 1.79-1.42 (m, 4H), 1.19-0.89 (m, 2H), 0.98 (s, 12H), 0.79 (d, J=6.4 Hz, 6H), 0.87-0.57 (m, 4H), 0.50-0.15 (m,4H). $^{13}$C NMR (75 MHz, CDCl$_3$) δ 33.46, 30.34, 29.84, 29.70, 22.64, 21.43, 18.27, 17.62, 15.72. $^{11}$B NMR (96 MHz, CDCl$_3$) δ 49.45, 0.31. HRMS (EI) calcd for C$_{20}$H$_{36}$BN [M]$^+$: 301.2935, found 301.2936.

4,7,7-Trimethylbicyclo[4.1.0]heptan-3-ol (4q), 84% yield. Clear, colorless liquid. $^1$H NMR (300 MHz, CDCl$_3$) δ 3.07 (td, J=9.7, 6.8 Hz, 1H), 2.10 (dd, J=14.0, 6.6 Hz, 1H), 1.97 (m, 1H), 1.75 (s, 1H), 1.57 (m, 1H), 1.30-1.13 (m, 1H), 1.05-0.97 (m, 1H), 0.97 (s, 3H), 0.92 (d, J=6.4 Hz, 3H), 0.90 (s, 3H), 0.88-0.65 (m, 2H). $^{13}$C NMR (75 MHz, CDCl$_3$) δ 74.95, 36.85, 30.90, 29.20, 28.81, 22.27, 20.51, 18.19, 18.03, 16.35.

Representative procedure for the synthesis of (±)-hydroxybenzoin (16a).

To a dry 25 mL round bottom flask containing a magnetic stir bar was added 0.124 g ammonia borane (4 mmol, 2 equiv), 0.357 g diphenylacetylene (14a, 2 mmol, 1 equiv), and 2 mL THF. The flask was fitted with a water-cooled reflux condenser and the reaction mixture rapidly brought to reflux in an oil bath at 90° C. The reaction mixture was stirred for 2 h open to air, after which time an aliquot was analyzed by $^{11}$B NMR spectroscopy, which showed several unresolvable signals centered at δ-5 ppm in addition to residual ammonia borane. The reaction mixture was cooled in an ice-water bath and oxidized with the addition of 1.3 mL 3 M NaOH (4 mmol, 2 equiv), followed by the of 1.4 mL 30% H$_2$O$_2$ (12.4 mmol, 6.2 equiv). The reaction contents were allowed to warm to room temperature with continued stirring for 3 h. The reaction mixture was extracted with ethyl acetate, the combined organic extracts dried over sodium sulfate, and concentrated in vacuo. The crude product was purified via silica gel chromatography to furnish 0.334 g (±)-hydroxybenzoin (16a) in 78% yield.

The generality of this reaction was extended to various other common hydroborating reagents. Generation of ammonia borane in situ from sodium borohydride and ammonium sulfate in THF proceeded as with pre-synthesized ammonia borane, with isolation of 16a in 83% yield.

(±)-hydrobenzoin (16a) White, crystalline solid. $^1$H NMR (300 MHz, Chloroform-d) δ 7.35-6.91 (m, 10H), 4.77 (s, 0.1H, meso contaminant), 4.62 (s, 2H), 3.23 (br s, 2H). $^{13}$C NMR (75 MHz, Chloroform-d) δ 139.4, 127.9, 127.6, 127.1, 79.2.

Those skilled in the art will recognize that numerous modifications can be made to the specific implementations described above. The implementations should not be limited to the particular limitations described. Other implementations may be possible.

It is intended that the scope of the present methods be defined by the following claims. It should be understood by those skilled in the art that various alternatives to the embodiments described herein may be employed in practicing the claims without departing from the spirit and scope as defined in the following claims.

What is claimed is:

1. A process for preparing an alcohol, primary, secondary, or vicinal diol using an alkene or alkyne, comprising the steps of a. preparing a solution of an ammonia borane (AB);
b. adding an alkene or alkyne to said AB solution;
c. refluxing with heating and stirring to afford an organoborane, wherein the effectiveness of this process is not affected by the presence of air or moisture;
d. cooling the reaction mixture to about 0° C. and then adjusting the pH of the solution to basic with a NaOH solution; and
e. oxidizing said organoborane by adding about three equivalents of $H_2O_2$ to afford an alcohol.

2. The process of claim 1, wherein the molar ratio of said AB to said alkene or alkyne ranges from about 2 to about 0.2.

3. The process of claim 1, wherein the molar ratio of said AB to said alkyne is about 2 for a vicinal diol.

4. The process of claim 1, wherein the molar ratio of said AB to said alkene is about 0.3 for a primary alcohol.

5. The process of claim 1, wherein the molar ratio of said AB to said alkene is about 0.5 for a secondary alcohol.

6. The process of claim 1, wherein said solution of an ammonia borane is prepared using THF (tetrahydrofuran).

7. The process of claim 6, wherein said ammonia borane in THF has a concentration of about 0.5~2 M (moles/liter).

8. The process of claim 1, wherein said refluxing is performed at about 90° C.

9. The process of claim 1, wherein said alkene or alkyne is part of an aromatic molecule, an aliphatic molecule, or a combination thereof.

10. The process of claim 1, wherein said alkene or alkyne is part of a cyclic structure, a linear structure, a branched structure, or a combination thereof.

* * * * *